US010322992B2

(12) United States Patent
Kadi et al.

(10) Patent No.: US 10,322,992 B2
(45) Date of Patent: Jun. 18, 2019

(54) METHODS OF MAKING CERIUM OXIDE POLYANILINE COMPOSITE NANOSPHERES AND METHODS OF USE

(71) Applicant: King Abdulaziz University, Jeddah (SA)

(72) Inventors: Mohammad W. Kadi, Jeddah (SA); R. M. Mohamed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 262 days.

(21) Appl. No.: 15/377,073

(22) Filed: Dec. 13, 2016

(65) Prior Publication Data

US 2018/0162801 A1    Jun. 14, 2018

(51) Int. Cl.
| | |
|---|---|
| *C07C 209/36* | (2006.01) |
| *B01J 23/10* | (2006.01) |
| *B01J 31/26* | (2006.01) |
| *B01J 31/06* | (2006.01) |
| *B01J 35/00* | (2006.01) |
| *B01J 37/04* | (2006.01) |
| *B01J 37/08* | (2006.01) |
| *B01J 13/02* | (2006.01) |
| *B01J 35/08* | (2006.01) |

(52) U.S. Cl.
CPC ............. *C07C 209/36* (2013.01); *B01J 13/02* (2013.01); *B01J 23/10* (2013.01); *B01J 31/26* (2013.01); *B01J 35/004* (2013.01); *B01J 35/008* (2013.01); *B01J 35/0013* (2013.01); *B01J 37/086* (2013.01); *B01J 31/06* (2013.01); *B01J 35/08* (2013.01); *B01J 2231/641* (2013.01); *B01J 2231/643* (2013.01); *B01J 2531/002* (2013.01); *B01J 2531/008* (2013.01); *B01J 2531/38* (2013.01)

(58) Field of Classification Search
None
See application file for complete search history.

(56) References Cited

FOREIGN PATENT DOCUMENTS

| | | | |
|---|---|---|---|
| CN | 1207264 | C | 6/2005 |
| CN | 102175735 | B | 4/2013 |
| CN | 104629071 | A * | 5/2015 |
| IN | 249974 | | 2/2009 |
| JP | 45232755 | B2 | 6/2010 |

OTHER PUBLICATIONS

Wei et al., "Hollow Microspheres of Polyaniline Synthesized with an Aniline Emulsion Template", Adv. Matr. 14, No. 18, pp. 1314-1317, 2002.*

Shaoxu Wang, et al., "Thermal stability of several polyanilinelrare earth oxide composites (I): polyaniline/$CeO_2$composites" Journal of Thermal Analysis and Calorimetry, vol. 107, Issue 3, Mar. 2012, pp. 1199-1203 (Abstract only).

Chuang Fy, et al., "Cerium dioxide/polyaniline core-shell nano composites", J. Colloid Interface Sci., vol. 320. No. 1, Apr. 1, 2008, pp. 194-201 (Abstract only).

M. Alhoshan, et al., "Optical and electrical properties of electrochemically deposited polyaniline/$CeO_2$ hybrid nanocomposite film", Journal of Semiconductors. vol. 32, No. 4, Apr. 2011, 6 pages.

"Reduction of nitro compound by using nano Pd/$CeO_2$ catalyst", Heterogeneous Catalysis for Degradation of Pesticide and Organic Transformations, Chapter IV, Dec. 5, 2015, 33 pages.

Bilge Özbay, et al., "Photocatalytic activities of polyaniline-modified $TiO_2$ and ZnO under visible light: an experimental and modeling study", Clean Techn Environ Policy, vol. 18, Issue 8, Dec. 2016, pp. 2591-2601.

Sadia Ameen, et al., "An effective nanocomposite of polyaniline and ZnO: preparation, characterizations, and its photocatalytic activity", Colloid Polym Sci., vol. 289, 2011, pp. 415-421.

Surbhi Sharma, et al., "Synthesis of polyaniline/CdS (nanoflowers and nanorods) nanocomposites: a comparative study towards enhanced photocatalytic activity for degradation of organic dye", Colloid Polym Sci., vol. 294, 2016, pp. 917-926.

Shixiong Min, et al., "An investigation on synthesis and photocatalytic activity of polyaniline sensitized nanocrystalline $TiO_2$ composites", J Mater Sci., vol. 42, 2007, pp. 9966-9972.

Yang Cheng, et al., "Simplified synthesis of polyaniline-TiO2 composite nanotubes for removal of azo dyes in aqueous solution", Res Chem Intermed, vol. 39, 2013, pp. 3969-3979.

Yang Cheng, et al., "Preparation of Polyaniline/$TiO_2$ Composite Nanotubes for Photodegradation of AZO Dyes", Journal of Wuhan University of Technology-Mater Sci. Ed., vol. 29. No. 3, Jun. 2014. pp. 468-472.

Jianhong Wei, et al., "Synthesis and photocatalytic activity of polyaniline-$TiO_2$ composites with bionic nanopapilla structure", J Nanopart Res., vol. 13, 2011, pp. 3157-3165.

Ali Olad, et al., "Preparation, characterization and photocatalytic activity of $TiO_2$/polyaniline core-shell nanocomposite", Bull. Mater. Sci., vol. 35, No. 5, Oct. 2012, pp. 801-809.

Shilpi Agarwal, et al., "Synthesis and characteristics of polyaniline/ zirconium oxide conductive nanocomposite for dye adsorption application", Journal of Molecular Liquids, vol. 218, 2015, pp. 494-498.

U.V. Patil, et al., "Room temperature ammonia sensor based on copper nanoparticle intercalated polyaniline nanocomposite thin films", Applied Surface Science, vol. 339, 2015, pp. 69-74.

R.V. Salvatierra, et al., "Carbon nanotubelpolyartiline nanocomposites: Electronic structure, doping level and morphology investigations", Synthetic Metals, vol. 203, 2015, pp. 16-21.

(Continued)

*Primary Examiner* — Kishor Mayekar
(74) *Attorney, Agent, or Firm* — Oblon, McClelland, Maier & Neustadt, L.L.P.

(57) ABSTRACT

Methods of synthesizing cerium oxide and polyaniline nanocomposites, including nanospheres enclosing a hollow core, are specified. Properties of the cerium oxide and polyaniline nanocomposites are described, as well as a method of using the nanocomposites as photocatalysts for the reduction of an aromatic nitro compound using visible light. A method for reusing the nanocomposites as photocatalysts is also discussed.

12 Claims, 20 Drawing Sheets

(56) References Cited

OTHER PUBLICATIONS

Tzia Ming Onn, et al., "Modification of Pd/$CeO_2$ catalyst by Atomic Layer Deposition of $ZrO_2$", Applied Catalysis B: Environmental, vol. 197, 2016, pp. 280-285.

Changjin Tang, et al., "Solid state preparation of NiO—$CeO_2$ catalyst for NO reduction", Catalysis Today, vol. 281, Part 3, 2016, pp. 575-582.

Tae-Hee Kim, et al., "Synthesis of $CeO_2$ nanocrystalline powders using DC non-transferred thermal plasma at atmospheric pressure", Advanced Powder Technology, 2016, 7 pages.

Yongjun He, "Synthesis of polyaniline/nano-$CeO_2$ composite microspheres via a solid-stabilized emulsion route", Materials Chemistry and Physics, vol. 92, 2005, pp. 134-137.

Feng-Yi Chuang, et al., "Cerium dioxide/polyaniline core-shell nanocomposites", Journal of Colloid and Interface Science, vol. 320, 2008, pp. 194-201.

E. Kumar, et al., "Preparation and characterization of polyanilineicerium dioxide ($CeO_2$) nanocomposite via in situ polymerization", J Mater Sci, vol. 47, 2012, pp. 7148-7156.

Y. Sasikumar, et al., "Hybrid nanocomposite from aniline and $CeO_2$ nanoparticles: Surface protective performance on mild steel in acidic environment", Applied Surface Science, vol. 330, 2015, pp. 207-215.

J.S.M. Da Silva, et al., "Chloride salt of conducting polyaniline synthesized in the presence of $CeO_2$: Structural analysis of the core-shell nanocomposite", Journal of Molecular Structure, vol. 1127, 2017, pp. 337-344.

\* cited by examiner

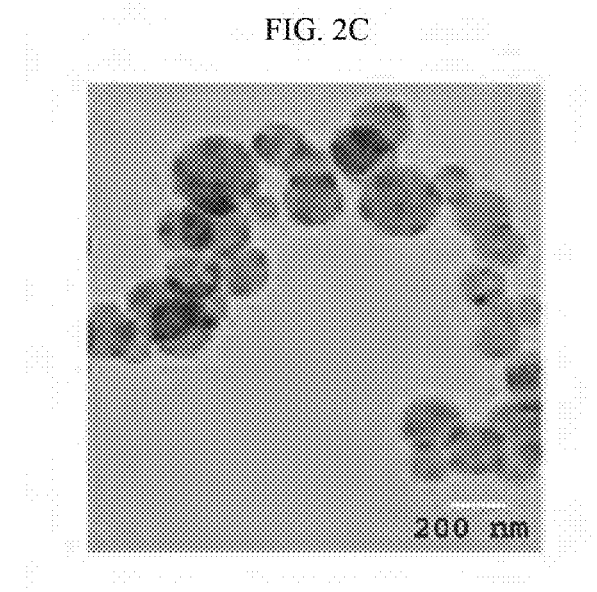

METHODS OF MAKING CERIUM OXIDE POLYANILINE COMPOSITE NANOSPHERES AND METHODS OF USE

BACKGROUND OF THE INVENTION

Technical Field

The present invention relates to a method of synthesizing nanospheres comprising a shell of cerium oxide and polyaniline composite surrounding a hollow core, and methods of use as a photocatalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Polyaniline (PANI) is a conjugated polymer that has attracted researcher's attention with its favorable properties towards photocatalysis and other applications. These properties include absorption of light in the visible range, environmental stability, high conductivity, and corrosion resistance. See Özbay, B. et al., Clean Techn Environ Policy, 18 (2016) 2597-2601, incorporated herein by reference in its entirety. Inorganic nano oxides such as $TiO_2$, ZnO, $CeO_2$, $WO_3$, and many others have been widely used in photocatalytic reactions. Researchers have tried to combine inorganic nanomaterials with organic polymers in efforts to prepare composites with high catalytic efficiency. For example, Ameen et al. synthesized a PANI ZnO composite and used it effectively in methylene blue dye degradation. See Ameen, S. et al., Colloid Polym Sci 289 (2011) 415-421, incorporated herein by reference in its entirety. Sharma et al. synthesized PANI/CdS nanocomposites of nanoflowers and nanorods and used them in photodegradation. See Sharma, S. et al., Colloid Polym Sci 294 (2016) 917-926, incorporated herein by reference in its entirety. Özbay et al. reported photocatalytic activities of polyaniline-modified. $TiO_2$ and ZnO under visible light. See Özbay, B. et al., Clean Techn Environ Policy, 18 (2016) 2597-2601, incorporated herein by reference in its entirety. Min et al. studied the photocatalytic activity of polyaniline sensitized nanocrystalline $TiO_2$ composites. See Min, S. et al., J Mater Sci 42 (2007) 9966-9972, incorporated herein by reference in its entirety. Many researchers have studied various structures of PANI and $TiO_2$ composites. These structures include nanotubes, bionic nanopapilla, and core shell structures. See Cheng, Y. et al., Res Chem Intermed 39 (2013) 3969-3979; Cheng, Y. et al., Journal of Wuhan University of Technology-Mater. Sci. Ed. 29 (2014) 468-472; Wei, J. et al., J Nanopart Res 13 (2011) 3157-3165; and Olad, A. et al., Bull. Mater. Sci. 35 (2012) 801-809, each incorporated herein by reference in its entirety. Agarwal reported preparation of a polyaniline/zirconium oxide conductive nanocomposite for dye adsorption applications. See Agarwal, S. et al., Journal of Molecular Liquids 218 (2016) 494-498, incorporated herein by reference in its entirety. Patil et al. developed a sensor for the detection of $NH_3$ utilizing copper nanoparticle intercalated polyaniline nanocomposite thin films. See Patil, U. V. et al., Applied Surface Science 339 (2015) 69-74, incorporated herein by reference in its entirety. Salvatierra et al. studied carbon nanotube/polyaniline nanocomposites. See Salvatierra, R. V. et al., Synthetic Metals 203 (2015) 16-21, incorporated herein by reference in its entirety.

$CeO_2$ is a good catalyst due to its redox properties and high oxygen storage capacity. See Onn, T. M. et al., Applied Catalysis B: Environmental 197 (2016) 280-285; Tang, C. et al., Catal. Today 281 (2017) 575-582; and Kim, T. H. et al., Advanced Powder Technology 27 (2016) 2012-2018, each incorporated herein by reference in its entirety. The combination of PANI and $CeO_2$ has also received attention. Yongjun He reported the synthesis of polyaniline/nano-$CeO_2$ composite microspheres via a solid-stabilized emulsion route. The synthesized polyaniline/nano-$CeO_2$ composite microspheres had an average diameter of 7 μm. See He, Y., Materials Chemistry, and Physics 92 (2005) 134-137, incorporated herein by reference in its entirety. Chuang and Yang used $CeO_2$ to oxidize aniline for the preparation of ($CeO_2$/PANI) core-shell nanocomposites. They reported a polygonal shape of the $CeO_2$/PANI nanocomposites. See Chuang, F. Y. and Yang, S. M., Journal of Colloid and Interface Science 320 (2008) 194-201, incorporated herein by reference in its entirety. Kumar et al. exploited in-situ polymerization to prepare the PANI/$CeO_2$ nanocomposite and reported the structure of this composite. See Kumar, E. et al., J Mater Sci 47 (2012) 7148-7156, incorporated herein by reference in its entirety. Sasikumar et al. reported the use of aniline, HCl, $CeO_2$ nanoparticles, ammonium persulfate, and water to synthesize PANI/$CeO_2$ composite, and they used it as a corrosion inhibitor. See Sasikumar, Y. et al., Applied Surface Science 330 (2015) 207-215, incorporated herein by reference in its entirety. Da Silva et al. reported preparation of a chloride salt of polyaniline ES-PANI in the presence of $CeO_2$. They concluded that a thin film of ES-PANI nanofibers covered the $CeO_2$ particles, forming a core-shell structure with non-uniform size and shape. See da Silva, J. S. M. et al., Journal of Molecular Structure 1127 (2017) 337-344, incorporated herein by reference in its entirety.

In view of the foregoing, one objective of the present invention is to provide a method for the preparation of a uniform core-shell spherical PANI $CeO_2$ nanocomposite and methods of use thereof.

BRIEF SUMMARY OF THE INVENTION

According to a first aspect, the present disclosure relates to a method of making cerium oxide and polyaniline composite nanospheres comprising a spherical shell, where each shell has a thickness of 5-60 nm and surrounds a hollow core having a 70-300 nm diameter. The method steps involve mixing aniline monomers with water, a first alcohol, and a surfactant to form a first mixture, adding an oxidizing agent to the first mixture to polymerize the aniline monomers to form polyaniline nanospheres, mixing the polyaniline nanospheres with a water soluble polymer, a cerium alkoxide, and a second alcohol to form a second mixture, and heating the second mixture at 300-400° C. to form the cerium oxide and polyaniline composite nanospheres.

In one embodiment, a molar ratio of the aniline monomers to the surfactant is 0.6-1.0.

In one embodiment, the surfactant is a sulfonic acid derivative.

In one embodiment, where the surfactant is a sulfonic acid derivative, the surfactant is sodium dodecylbenzenesulfonate.

In one embodiment, the first alcohol has a molecular weight of 30-140 g/mol and a boiling point of 60-180° C.

In a further embodiment, the first alcohol is n-butanol

In one embodiment, the oxidizing agent is ammonium persulfate, sodium persulfate, and/or potassium persulfate.

In one embodiment, the water soluble polymer is polyvinylpyrrolidone, and a mass ratio of the polyaniline nanospheres to polyvinylpyrrolidone in the second mixture is 3.0-8.0.

In one embodiment, the cerium alkoxide is cerium isopropoxide.

In one embodiment, a mass ratio of cerium to polyaniline nanospheres in the second mixture is 1.5-3.5.

In one embodiment, the cerium oxide and polyaniline composite nanospheres have a porous surface with a surface area of 220-300 $m^2/g$ and an average pore diameter of 1.5-5.0 nm.

In one embodiment, the cerium oxide and polyaniline composite nanospheres have a band gap energy of 1.75-2.05 eV.

According to a second aspect, the disclosure relates to a method of reducing an aromatic nitro compound into an aromatic amine compound with cerium oxide and polyaniline composite nanospheres. These cerium oxide and polyaniline composite nanospheres each comprise a spherical shell, wherein each shell has a thickness of 5-60 nm and surrounds a hollow core having a 70-300 nm diameter. The method involves mixing the cerium oxide and polyaniline composite nanospheres with the aromatic nitro compound in an alcohol solution to form a reaction solution, and irradiating the reaction solution with a light to photocatalytically convert the aromatic nitro compound into the aromatic amine compound.

In one embodiment, the light has a wavelength of 400-700 nm.

In one embodiment, a concentration of the aromatic nitro compound in the reaction solution is 0.1-3.0 mM.

In one embodiment, the aromatic nitro compound is nitrobenzene, and the aromatic amine compound is aniline.

In one embodiment, a concentration of the cerium oxide and polyaniline composite nanospheres in the reaction solution is 0.1-2.0 g/L.

In one embodiment, the alcohol is methanol.

In one embodiment, the aromatic amine compound is produced at a rate of 10-800 μmol/h per gram of the cerium oxide and polyaniline composite nanospheres.

In one embodiment, the method also involves recovering the cerium oxide and polyaniline composite nanospheres after the irradiating to produce recovered cerium oxide and polyaniline composite nanospheres and reusing the recovered cerium oxide and polyaniline composite nanospheres, which maintain photocatalytic activity for at least 4 reaction cycles.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2C is a TEM image of $CeO_2$_NS.

DETAILED DESCRIPTION OF THE EMBODIMENTS

Figure 1:
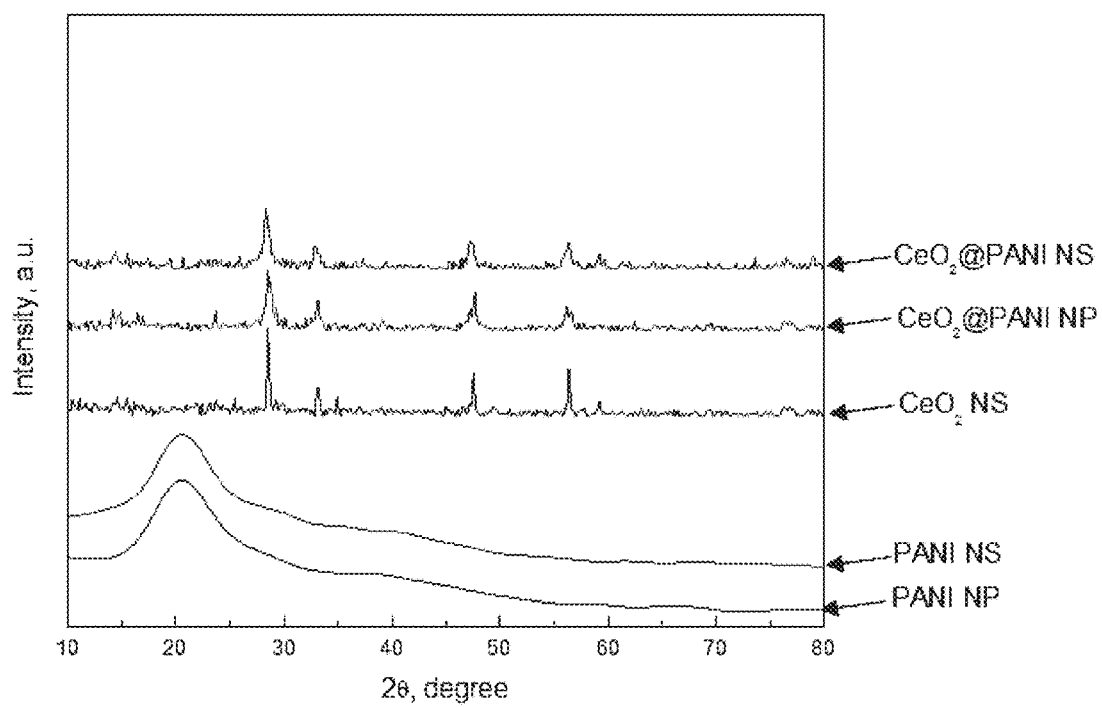
FIG. 1 shows X-ray diffraction patterns of PANI_NP, PANI_NS, $CeO_2$_NS, $CeO_2$@PANI_NP, and $CeO_2$@PANI_NS.

Embodiments of the present disclosure will now be described more fully hereinafter with reference to the accompanying figures, in which some, but not all embodiments of the disclosure are shown.

The present disclosure will be better understood with reference to the following terms and meanings set forth below. Unless defined otherwise, all technical and scientific terms used herein have the same meaning as commonly understood to one of ordinary skill in the art.

As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid. or gas, and whether in a crude mixture or isolated and purified.

As used herein, a "composite" is intended to refer to a solid material comprising more than one phase, structure, andior compound.

As used herein, a "nanocomposite" is intended to refer to a composite wherein the phase, structure, and/or compound domains have one or more dimensions of 100 nanometers (nm) or less, and/or repeat distances of 100 nm or less.

The term "alkyl", as used herein, unless otherwise specified, refers to a saturated straight, branched, or cyclic, primary, secondary, or tertiary hydrocarbon of typically C1 to C8, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, halogen, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

As used herein, the term "substituted" refers to at least one hydrogen atom that is replaced with a non-hydrogen group, provided that normal valencies are maintained, and that the substitution results in a stable compound.

The term "alkoxide," as used herein, refers to an alkyl—O— group wherein alkyl is as previously described. Example groups include, but are not limited to, methoxide, ethoxide, propoxide, isopropoxide, butoxide, i-butoxide, and pentoxide.

The term "aromatic compound," as used herein, refers to an organic compound comprising at least one unsaturated cyclic group having delocalized π electrons. The term is intended to encompass both hydrocarbon aromatic compounds and heteroaromatic compounds. The term "hydrocarbon aromatic compound" refers to an aromatic compound in which the aromatic moieties have only carbon and hydrogen atoms. The term "heteroaromatic compound" refers to a compound wherein in at least one aromatic moiety or one or more of the carbon atoms within the cyclic group has been replaced by another atom, such as nitrogen, oxygen, sulfur, or the like.

The term "aromatic nitro compound" refers to an aromatic compound having at least one nitro functional group ($-NO_2$).

The present disclosure is intended to include all isotopes of atoms occurring in the present compounds and complexes. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

In a first embodiment, the present disclosure relates to a method of making cerium oxide and polyaniline composite nanospheres. Here, in one embodiment, substituted or unsubstituted aniline monomers may be mixed with water, a first alcohol, and a surfactant to form a first mixture. A substituted aniline monomer refers to an aniline having a hydrogen replaced by a non-hydrogen group, following the previously mentioned definition of "substituted." Preferably the non-hydrogen group does not prevent polymerization of the substituted aniline monomers. The non-hydrogen group includes, but is not limited to, halogens, alkyls, alkoxyls, haloalkyls, carboxyls, carbamyls, cyanos, sulfonyls, and thiols. Examples of substituted aniline monomers include, but are not limited to, N-ethylaniline, 2-fluoroaniline, 2-chloroaniline, 2-methylaniline, 3-methylaniline, 2-methoxyaniline, 3-methoxyaniline, 2-ethoxyaniline, 3-ethoxyaniline, 1,3-diaminobenzene, and aniline-2-sulfonic acid. In one embodiment, the substituted aniline monomers may polymerize to form substituted polyaniline. In another embodiment, unsubstituted aniline monomers may be mixed with one or more types of substituted aniline monomers in order to form a polymer of both substituted and unsubstituted aniline subunits. The mass percentage of aniline in the first mixture may be 0.1-3%, preferably 0.5-2%, more preferably 0.9-1.5%. The concentration of first alcohol in the mixture may be 0.1-0.7 M, preferably 0.2-0.6 M, more preferably 0.3-0.5 M. The mass of the first alcohol may be a percentage of the mass of the water; this percentage may be 1-6%, preferably 2-5%, more preferably 3-4%. The first alcohol may be methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol cyclopropylmethanol, cyclopropanol, cyclobutanol, cyclopentanol, cyclohexanol, and/or some other alcohol. In one embodiment, the first alcohol has a molecular weight of 30-140 g/mol, preferably 50-110 g/mol, more preferably 70-80 g/mol and a boiling point of 60-180° C. preferably 8-155° C, more preferably 110-125° C. In one embodiment, the first alcohol is n-butanol.

The molar ratio of the aniline monomer to the surfactant may be 0.6-1.0, preferably 0.65-0.9, more preferably 0.7-0.9. The surfactant may be an anionic surfactant, such as sodium dodecylbenzene sulfonate (SDBS), sodium dodecyl sulfate (SDS), sodium laurate, sodium laureth sulfate (SLES), sodium lauryl sulfate (SLS), ammonium lauryl sulfate (ALS), sodium pareth sulfate, potassium lauryl sulfate, sodium nonanoyloxybenzenulfonate (NOBS), sodium stearate, magnesium laureth sulfate, sodium myreth sulfate, and/or some other anionic surfactant. In one embodiment, a cationic, non-ionic, or zwitterionic surfactant may be used instead of an anionic surfactant. In one embodiment, the surfactant may be a sulfonic acid derivative, such as a compound containing a sulfonate, a sulfonamide, and the like. In one embodiment, the surfactant is sodium dodecylbenzene sulfonate (SDBS). The SDBS molecules may comprise dodecyl chains that are branched, linear, or a mixture of both. Preferably the benzene is para-substituted, however, in some embodiments the benzene may be meta or ortho-substituted. For example, SDBS with a linear dodecyl chain and a para-substituted benzene may be sodium 4-(5-dodecyl) benzenesulfonate. SDBS with a branched dodecyl chain and a meta-substituted benzene may be sodium 3-(3-(4,5,6-trimethylnonane) benzenesulfonate. In other embodiments, the dodecylbenzene sulfonate may have a different counter ion, for example, potassium.

Preferably in forming the first mixture, the surfactant may first be dissolved in the water while maintaining a low pH by the addition of a concentrated acid. The resulting pH may be 0.1-3, preferably 0.1-2, more preferably 0.2-0.5. The concentrated acid may be hydrochloric acid, bromic acid, sulfuric acid, nitric acid, iodic acid, hydrofluoric acid, and/or some other acid. The aniline may then be added and may be stirred or agitated for at least 10 minutes, preferably at least 30 minutes, more preferably at least 50 minutes, though in an alternative embodiment, the mixture is not stirred or agitated. Next, the alcohol may be added, preferably dropwise or in small increments, in order to form the first mixture.

An oxidizing agent may then be mixed with the first mixture. The molar ratio of the oxidizing agent to the aniline monomer may be 1:5-5:1, preferably 1:2-2:1, more preferably 1:1.5-1.5:1, even more preferably 1:1.1-1.1:1. The oxidizing agent may be mixed directly with the first mixture, or the oxidizing agent may be dissolved in water and then mixed with the first mixture. The oxidizing agent may be sodium peroxide, sodium hypochlorite, hydrogen peroxide, sodium perborate, sodium percarbonate, potassium chlorite, potassium periodate, potassium iodate, tert-butyl hydroperoxide, benzoyl peroxide, potassium bichromate iron(III) chloride, potassium permanganate, potassium bromate, potassium chlorate, a persulfate salt, potassium biiodate, and/or some other oxidizing agent. In one embodiment, the oxidizing agent may be a persulfate salt, such as ammonium persulfate, sodium persulfate, and/or potassium persulfate. In a preferred embodiment, the oxidizing agent may be ammonium persulfate, and may be in an aqueous solution at a 5-30%, 5-20%, 5-15%, or about 10% mass concentration before mixing.

The temperature may be adjusted to 20-35° C., preferably 22-30° C., more preferably 23-28° C. and maintained at that temperature or temperature range while stirring or agitating for at least 2 hours, preferably at least 3 hours, more preferably at least 5 hours. Preferably the oxidizing agent reacts with the aniline monomers to form polyaniline, and in the presence of the surfactant, the polyaniline may be adsorbed to and/or incorporated within micelles formed from the surfactant. The aniline may change from a yellow or a dark yellow color to a green or a dark green color upon polymerization. The polyaniline may be recovered as polyaniline nanospheres, and washed with water and an alcohol. The alcohol may be any of those listed previously, but preferably the alcohol is ethanol. The polyaniline nanospheres may be dried in a vacuum oven for at least 2 hours, preferably at least 8 hours, more preferably at least 12 hours at a temperature of 50-100° C., preferably 55-90° C., more preferably 60-80° C., and at an absolute pressure of 0.001-10 mbar, preferably 0.001-1 mbar, more preferably 0.001-0.5 mbar. In an alternative embodiment, the polyaniline nanospheres may be dried under a vacuum at room temperature or in an oven at atmospheric pressure. The polyaniline may have an average MW of preferably 1-400 kDa, preferably 5-300 kDa, more preferably 20-200 kDa. Molecules of polyaniline may comprise aniline units of different oxidation states. For example, the polyaniline could be in the form of leucoemeraldine, where the aniline units are fully reduced and are thus connected by amine groups. Alternatively, the polyaniline could in the form of pernigraniline, where the aniline units are in a fully oxidized state and are thus connected by imine groups. Alternatively, the polyaniline could be in the form of emeraldine, which comprises aniline units in both oxidation states where 30-70%, preferably 40-60%, more preferably 45-55% of the aniline units are oxidized with the remaining aniline units being reduced. Preferably, the majority of the polyaniline is in the form of emeraldine, with the imine groups protonated to form an emeraldine salt. Preferably each polyaniline nanosphere comprises a hollow core which is surrounded by a shell of polyaniline. This polyaniline shell may surround greater than 60%, preferably greater than 80%, more preferably greater than 98% of the hollow core. In a preferred embodiment, each polyaniline shell surrounds 100% of a hollow core, meaning that the hollow core is completely enclosed by the polyaniline shell. Preferably, following the drying, the hollow cores contain air. The term "hollow core" does not necessarily mean a core devoid of matter (i.e., a vacuum). In some embodiments, the polyaniline shells may be permeable or semipermeable, and the hollow cores may comprise one or more compounds of the current environment, and/or one or more compounds that have been used in a previous reaction step. Preferably these compounds are liquids or gases. Polyaniline nanospheres formed by the same method may have hollow cores comprising different compounds if placed in different environments. Preferably the polyaniline shell has a substantially uniform thickness, meaning that the thickness of the polyaniline shell at any part deviates from the average thickness by an amount less than 10 nm, preferably less than 8 nm, more preferably less than 5 nm. In an alternative embodiment, the shell may have an ellipsoidal, an oblong, an ovoid, or some other rounded shape. The polyaniline nanospheres may have an average surface area of 160-240 $m^2/g$, preferably 170-230 $m^2/g$, even more preferably 180-220 $m^2/g$, an average shell thickness of 5-60 nm, preferably 10-50 nm, even more preferably 20-46 nm, and an average hollow core diameter of 130-210 nm, preferably 150-190 nm, more preferably 155-185 nm.

The polyaniline nanospheres may be mixed with a water soluble polymer, a second alcohol, and a cerium alkoxide to form a second mixture. The mass ratio of the polyaniline nanospheres to the water soluble polymer in the second mixture may be 3.0-8.0, preferably 3.5-7.5, more preferably 4.5-6.5. The mass ratio of the second alcohol to the polyaniline nanospheres may be 7-25, preferably 10-20, more preferably 13.5-16.5. Preferably the mass of the polyaniline nanospheres in the second mixture is equivalent to the total mass of the polyaniline in the second mixture. The second alcohol may be any of those listed previously, but preferably the second alcohol may be ethanol. The mixture of the second alcohol and polyaniline nanospheres may be dispersed by sonicating in a bath for at least 10 minutes, preferably at least 30 minutes, more preferably at least 60 minutes, or the polyaniline nanospheres may be dispersed by some other means, such as stirring, shaking, or inserting a sonication probe into the solution. In one embodiment, the nanospheres may be mixed with the second alcohol without further dispersing.

The mass ratio of the cerium to the polyaniline nanospheres may be 1.5-3.5, preferably 2.0-3.2, more preferably 2.4-2.8. Preferably the mass of the polyaniline nanospheres is equivalent to the mass of the polyaniline. The cerium alkoxide may be mixed directly or may be in the form of a solution before being mixed with the polyaniline nanospheres. Where the cerium alkoxide is in a solution before being mixed, its concentration in the solution may be 0.05-0.8 M, preferably 0.1-0.6 M, more preferably 0.2-0.4 M. Preferably the solvent of this solution comprises ethanol, but the solvent could be any of the previously mentioned alcohols, or some other organic solvent, such as chloroform.

In one embodiment, the cerium alkoxide may be cerium isopropoxide. However, in other embodiments, the cerium alkoxide may be cerium ethoxide, cerium methoxide, cerium butoxide, cerium propoxide, cerium pentoxide, and/or some other cerium alkoxide. In one embodiment, more than one type of cerium alkoxide may be used in the reaction. For instance, a mixture of cerium propoxide and cerium isopropoxide may have a molar ratio of 10:1-1:10, preferably 2:1-1:2, more preferably 1.1:1-1:1.1, and a certain volume may be used to achieve a preferred mass ratio of cerium to polyaniline nanospheres as mentioned previously. In one alternative embodiment, the polyaniline nanospheres may be obtained by a different technique or synthesis method. In one embodiment, the water soluble polymer may be polyvinylpyrrolidone (PVP), polyethylene glycol (PEG), polyvinyl pyrrolidone vinyl acetate (PVP-VA) copolymer, polyvinyl alcohol (PVA), polyacrylic acid (PAA), polyacrylamide, polyethylenimine (PEI), chitosan, dextran, hyaluronic acid, DNA, a polypeptide, and/or some other polymer. Preferably the water soluble polymer is polyvinylpyrrolidone (PVP) with an average molecular weight of 5-400 kDa, preferably 10-100 kDa, more preferably 30-50 kDa.

The cerium alkoxide, second alcohol, water soluble polymer, and polyaniline nanospheres of the second mixture may be dispersed and/or reacted by sonicating in a bath or with a sonication probe for at least 30 minutes, preferably at least 1 hour, more preferably at least 3 hours. In one embodiment, the second mixture may be stirred or agitated instead of sonicated, though in one embodiment, the second mixture may react without stirring, agitating, or sonicating. The nanospheres may be recovered and washed with water and/or an alcohol. These nanospheres may be dried for at least 4 hours, preferably at least 12 hours, more preferably at least 24 hours at a temperature of 80-120° C., preferably 90-110° C., preferably 95-105° C. In one embodiment, the nanospheres may be washed and/or dried while under a vacuum, which may be at an absolute pressure of 0.001-10 mbar, preferably 0.001-1 mbar, more preferably 0.001-0.5 mbar. The nanospheres may then be calcined for 2-8 hours, preferably 3-7 hours, more preferably 3.5-6 hours at a temperature of 300-400° C., preferably 320-380° C., more preferably 330-370° C. In one embodiment, the nanospheres may be alcined at higher temperatures, for example, 400-650° C. Fallowing the calcination, the nanospheres may be in the form of cerium oxide and polyaniline composite nanospheres. In one embodiment, the cerium oxide is fmmed from the cerium alkoxide. In another embodiment, pre-formed cerium oxide nanoparticles are not used to form the cerium oxide and polyaniline composite nanospheres. In another embodiment, cerium hydroxide, cerium oxalate, cerium metal, cerium nitrate and/or ammonium cerium nitrate are not used to form the cerium oxide and polyaniline composite nanospheres. Preferably the cerium oxide is cerium(IV) oxide ($CeO_2$), though in some embodiments, less than 5 mol %, preferably less than 1 mol %, more preferably less than 0.5 mol % of the cerium oxide may be cerium(III) oxide ($Ce_2O_3$). In one embodiment, all of the cerium oxide is cerium(IV) oxide ($CeO_2$).

These cerium oxide and polyaniline composite nanospheres formed may comprise a spherical shell of a cerium oxide and polyaniline nanocomposite surrounding a hollow core. The hollow core may have a diameter of 70-300 nm, 90-250 nm, 130-220 nm, or preferably 180-200 nm. The nanocomposite shell may have a thickness of 5-60 nm, 10-57 nm, 15-55 nm, or preferably 22-52 nm. The nanocomposite shell may surround greater than 60%, preferably greater than 80%, more preferably greater than 98% of the hollow core. In a preferred embodiment, the nanocomposite shell surrounds 100% of the hollow core, meaning that the hollow core is completely enclosed by the nanocomposite shell. Preferably, following the drying and/or calcination, the hollow cores contain air. As mentioned previously, the term "hollow core" does not necessarily mean a core devoid of matter (i.e., a vacuum). In some embodiments, the nanocomposite may be permeable or semipermeable, and the hollow cores may comprise one or more compounds of the current environment, and/or one or more compounds that have been used in a previous reaction step. Preferably these compounds are liquids or gases. Cerium oxide and polyaniline composite nanospheres formed by the same method may have hollow cores comprising different compounds if placed in different environments. Preferably the nanocomposite shell has a substantially uniform thickness, meaning that the thickness of the nanocomposite shell at any part deviates from the average thickness by an amount less than 10 nm, preferably less than 8 nm, more preferably less than 5 nm. In an alternative embodiment, the nanocomposite shell may have an ellipsoidal, an oblong, an ovoid, or some other rounded shape. As mentioned, the nanocomposite shell may comprise a composite of cerium oxide and polyaniline. The cerium oxide may be in the form of nanoparticles with an average diameter of 2-50 nm, 3-40 nm, 4-30 nm, or preferably 5-20 nm. The nanospheres may comprise 50-90%, 60-85%, preferably 60-75% cerium oxide by mass, with the remaining mass comprising polyaniline. The cerium oxide and polyaniline composite nanospheres may comprise polyaniline with an oxidation state and molecular weight as mentioned previously for the polyaniline nanospheres. In one embodiment, the deposition of the cerium oxide does not change the average molecular weight of the polyaniline. Preferably, the cerium oxide and polyaniline are evenly dispersed to form the nanocomposite shell, though in one embodiment, a higher density of cerium oxide may exist on and/or within an outer portion of the nanocomposite shell while a higher concentration of polyaniline exists on and/or within an interior portion of the nanocomposite shell, or vice versa. In an alternative embodiment, the cerium oxide may be present as agglomerates of particles within a polyaniline layer enclosing a hollow core. As used herein, the term "agglomerates" refers to a clustered particulate composition comprising primary particles, the primary particles being aggregated together in such a way so as to form clusters thereof, at least 50 volume percent of the clusters having a mean diameter that is at least 2 times the mean diameter of the primary particles, and preferably at least 90 volume percent of the clusters having a mean diameter that is at least 5 times the mean diameter of the primary particles. The primary particles may be cerium oxide nanoparticles having an average diameter as mentioned previously. These agglomerates may have a largest dimension of 4-50 nm, preferably 6-40 nm, more preferably 8-20 nm. The cerium oxide and polyaniline composite nanospheres may be mesoporous or macroporous. The term "microporous" means a surface having an average pore diameter of less than 2 nm, while the term "mesoporous" means a surface having an average pore diameter of 2-50 nm. In one embodiment, the cerium oxide and polyaniline composite nanospheres may have an average pore diameter of 1.5-5.0 nm, preferably 1.8-4.8 nm, more preferably 2.0-4.5 nm. In another embodiment, the cerium oxide and polyaniline composite nanospheres may have a surface area of 220-300 $m^2/g$, preferably 240-280 $m^2/g$, more preferably 250-270 $m^2/g$. In another embodiment, the cerium oxide and polyaniline composite nanospheres may have a band gap energy of 1.75-2.05 eV, preferably 1.85-2.00 eV, more preferably 1.90-1.95 eV. This band gap energy may also be known as the "electronic" or "electrical" band gap energy. The surface area may be determined by measuring gas adsorption on the surface of the particles using BET theory calculations, or by using flow deflection, gravimetric techniques, or other methods. The band gap energy may be determined by a UV-Vis adsorption spectrum, or by photoluminescence measurements.

According to a second aspect, the present disclosure relates to a method of reducing an aromatic nitro compound into an aromatic amine compound using cerium oxide and polyaniline composite nanospheres. These cerium oxide and polyaniline composite nanospheres may comprise a spherical shell of a cerium oxide and polyaniline nanocomposite surrounding a hollow core, with dimensions as described previously. The cerium oxide and polyaniline composite nanospheres may have similar properties as described for those in the first aspect, such as band gap energy, surface area, and/or some other property. In other embodiments, the cerium oxide and polyaniline composite nanospheres may have one or more dissimilar properties as compared to those described in the first aspect. For example, cerium oxide and polyaniline composite nanospheres may be used which have a hollow core with a diameter smaller than 70 nm or greater than 300 nm, and/or a shell thickness smaller than 5 nm or greater than 60 nm. Alternatively, cerium oxide and polyaniline composite nanospheres may be used which have band gap energies lower than 1.75 eV or higher than 2.05 eV. These cerium oxide and polyaniline composite nanospheres with dissimilar properties may be formed by using reagents, such as surfactant, aniline, or cerium alkoxide, that are at different concentrations than those described previously. Alternatively, these cerium oxide and polyaniline composite nanospheres with dissimilar properties may be formed by changing reaction conditions, such as time and/or temperature.

In one embodiment, the cerium oxide and polyaniline composite nanospheres may be synthesized by the previously described method of the first aspect, or they may be obtained by some other method. For example, cerium oxide nanoparticles may be used as a starting material to which aniline is added and polymerized, creating, a core-shell nanoparticle. Alternatively, cerium oxide and polyaniline composite nanospheres may be formed by a solid-stabilized emulsion method or by in-situ polymerization of aniline. Returning to the embodiment of the disclosure, the cerium oxide and polyaniline composite nanospheres may be mixed with an aromatic nitro compound and an alcohol to form a reaction solution. The aromatic nitro compound may be a nitrophenyl, a nitrophenol, a nitro-benzimidazole, a nitropyridinyl, a nitro-bipyridine, a nitro-phenoxyl, a nitro-indazole, a nitroaniline, a nitrotoluene, a nitrobenzamide, a nitro-benzoic acid, a nitro-carbazole, a nitro-benzotriazole, a nitro-benzoxazole, and/or some other aromatic nitro compound in substituted or unsubstituted forms. In one embodiment, the aromatic nitro compound is nitrobenzene. The alcohol may be any of those previously listed; preferably the alcohol is methanol. The aromatic nitro compound may be present in the reaction solution at a concentration of 0.1-3.0 mM, preferably 0.4-2.0 mM, more preferably 0.6-1.0 mM. The cerium oxide and polyaniline composite nanospheres or nanoparticles may be present in the reaction solution at a concentration of 0.1-2.0 g/L, preferably 0.8-1.6 g/L, more preferably 1.0-1.4 g/L. The reaction solution may be sonicated, stirred, or agitated to evenly disperse the cerium oxide and polyaniline composite nanospheres, though in one embodiment, the nanospheres are not dispersed. The reaction solution may be flushed with an inert gas, such as nitrogen or argon, in order to displace and remove dissolved oxygen gas. The reaction solution may be irradiated with a light source to photocatalytically convert the aromatic nitro compound into an aromatic amine compound, and may be irradiated for 0.5-6 hours, preferably 1-4 hours, more preferably 1.5-3 hours.

The irradiation source may be a flame, a lantern, a gas discharge lamp, an incandescent bulb, a laser, a fluorescent lamp, an electric arc, a light emitting diode (LED), a cathode ray tube, sunlight, and/or some other source of light. The irradiation source may emit light within the ultraviolet, visible, or infrared wavelength ranges, which together span from 120 nm to 1 mm. Preferably the irradiation source emits broad wavelength light which comprises a portion or all of the visible light spectrum, where the visible light spectrum comprises wavelengths of 400-700 nm. In one embodiment, a filter may be used to prevent UV light from entering the solution, for example, a filter that blocks light with wavelengths less than 420 nm may be used with a xenon or mercury gas discharge lamp. Alternatively, a light source may be used which only emits light within the visible spectrum. In one embodiment, the reaction solution is irradiated with light having one or more wavelengths of 400-700 nm, and may or may not have wavelengths below 400 nm and/or above 700 nm. In a preferred embodiment, a xenon gas discharge lamp may be used with an optical filter with a cut-off wavelength of 420 nm in order to irradiate the reaction solution with visible light while attenuating or blocking light from the UV spectrum. The light source may emit a total of 50-1000 W, preferably 100-750 W, more preferably 250-600 W, and may be positioned 5-30 cm, preferably 7-20 cm, more preferably 8-15 cm from the closest surface of the reaction solution. Where a light source emits heat, the reaction solution may be temperature-regulated to prevent overheating and/or evaporation, for example, by water tubing, a water and/or ice bath, ice packs, or by air cooling. In a preferred embodiment, the reaction solution is maintained at 22-37° C., preferably 25-35° C., more preferably 28-32° C. To limit or prevent evaporation, the reaction solution may be in a sealed vessel or some other container, preferably with a transparent window. For example, the window may comprise glass or quartz, though in one embodiment, a polymeric material transparent to visible light and chemically stable with the reaction solution may be used. As defined herein, "transparent" refers to an optical quality of a compound wherein a certain wavelength or range of wavelengths of light may traverse through a portion of the compound with a small loss of light intensity. Here, the "transparent window" may causes a loss of less than 10%, preferably less than 5%, more preferably less than 2% of the intensity of a certain wavelength or range of wavelengths of light. In one embodiment, the vessel wall and window may comprise the same material, for example, a vessel may comprise quartz walls, which may also function as transparent windows. The reaction solution may be sonicated, stirred, or agitated while being irradiated, though in one embodiment, the reaction solution is left to sit while being irradiated.

In one embodiment, reflectors, fiber optics, polarizers, and/or lenses may be used to manipulate the light path or properties of the light. For example, one or more lenses may be used to focus the light within the reaction solution. Alternatively, a reflector may be positioned on the side of the vessel opposite the light source in order to reflect transmitted light back into the reaction solution. In one embodiment, two or more light sources may be used, which may be of the same type or different types, and may be positioned on the same side or on different sides of the reaction solution.

In other embodiments, an effective irradiation time may depend on several parameters, including, but not limited to wavelength, power, coherence, and density of emitted light, distance between the light source and the reaction solution, diffusion of the nanospheres or reagents within the reaction solution, the depth or thickness of the reaction solution, the concentration of catalyst, the concentration and type of the nitro-aromatic compound, the type of alcohol, and the material of the reaction vessel wall or window. A researcher having ordinary skill in the art may readily determine an effective irradiation method.

In an alternative embodiment, the reaction solution may be irradiated only with light from the UV spectrum. In an alternative embodiment, the light source may be sealed within a transparent capsule and submerged into the reaction solution.

The light irradiation of the reaction solution may induce the cerium oxide and polyaniline composite nanospheres to photocatalytically convert the aromatic nitro compound into an aromatic amine compound. Preferably the photocatalytic conversion reduces the nitro group of the aromatic nitro compound into an amine group, though in an alternative embodiment, other reactions may occur. Of the initial aromatic nitro compound, at least 50 mol %, preferably at least 70 mol %, more preferably at least 90 mol % may be converted into an aromatic amine compound. The aromatic amine compound may be an aniline, a phenolic amine, an amino benzimidazole, an aminopyridinyl, an aminobipyridine, ara amino-phenoxy, an aminoindazole, an aminotoluene, an aminobenzamide, an aminobenzoic acid, an aminocarbazole, an aminobenzotriazole, an aminobenzoxazole, and/or some other aromatic amine compound in substituted or unsubstituted forms. In one embodiment, a mixture of different aromatic nitro compounds may be converted into a mixture of different aromatic amine compounds. In an alternative embodiment, the cerium oxide and polyaniline composite nanospheres may catalyze an aromatic nitro compound into an aromatic amine compound without light irradiation but with high temperature, high pressure, or an electric current. In an alternative embodiment the cerium oxide and polyaniline composite nanospheres may catalyze other chemical processes, such as the reduction of a nitro-alkene compound.

In one embodiment, the aromatic nitro compound is nitrobenzene, and the aromatic amine compound is aniline. In one embodiment, the aromatic amine compound formed is dissolved in the reaction solution but may be quantified by gas chromatography. In an alternative embodiment, the aromatic amine compound may be separated from the reaction solution and purified. In one embodiment, the aromatic amine compound is produced at a rate of 10-800 µmol/h per gram of the cerium oxide and polyaniline composite nanospheres. This rate may be 50-750 $\mu mol \cdot h^{-1} \cdot g^{-1}$, preferably 100-700 $\mu mol \cdot h^{-1} \cdot g^{-1}$, more preferably 250-600 $\mu mol \cdot h^{-1} \cdot g^{-1}$, though in some embodiments, the aromatic amine compound may be produced at a rate greater than 800 $\mu mol \cdot h^{-1} \cdot g^{-1}$.

In one embodiment, following irradiation, the cerium oxide and polyaniline composite nanospheres may be separated from the reaction solution by filtering and/or centrifugation. These recovered cerium oxide and polyaniline composite nanospheres may be recycled and used as a photocatalyst in a second reaction solution. The recovered cerium oxide and polyaniline composite nanospheres may maintain photocatalytic activity for at least 4, preferably at least 8, more preferably at least 12 reaction cycles, and may or may not be washed and/or dried between reaction cycles. As defined here, "maintaining photocatalytic activity" means that when recycling and reusing the recovered cerium oxide and polyaniline composite nanospheres, the photocatalytic activity of producing the aromatic amine compound (as measured in $\mu mol \cdot g^{-1} \cdot h^{-1}$, as described previously) remains within at least 90%, preferably at least 95%, more preferably at least 96% of its original value.

In one alternative embodiment, the present disclosure relates to a method of making cerium oxide and polyaniline composite nanoparticles having diameters or largest widths of 50-100 nm, preferably 60-90 nm, more preferably 70-80 nm, and surface areas of 80-140 $m^{-2}/g$, preferably 90-130 $m^2/g$. These cerium oxide and polyaniline composite nanoparticles do not comprise hollow cores. Here, aniline monomers may be mixed with water and an inorganic acid to form an acidic solution comprising an aniline concentration of 0.5-2.0 w/w %, preferably 0.9-1.7 w/w %, more preferably 1.1-1.5 w/w %. The inorganic acid may be any of those listed previously. Preferably the inorganic acid is HCl. Preferably the inorganic acid is added to maintain the acidic solution at a pH of 0.1-3, preferably 0.1-2, more preferably 0.2-0.5. In one embodiment, the water and HCl may be stirred or agitated while the aniline is added, and in another embodiment, the solutions may be cooled in an ice water bath or instead cooled at 0-5° C., preferably 0.5-3° C., more preferably 0.5-2° C. An oxidizing agent may be mixed with the solution to achieve a molar ratio of oxidizing agent to aniline monomer of 1:3-3:1, preferably 1:1.5-1.5:1, more preferably 1:1.1-1.1:1. The oxidizing agent may be any of those listed previously, and may be mixed directly with the acidic solution or first dissolved in a separate solution before mixing with the acidic solution. Preferably the oxidizing agent may be arrmonium persulfate, and in a preferred embodiment, the ammonium persulfate may be dissolved in water at a 10% mass concentration before mixing, After mixing the oxidizing agent, the solution may be stirred or agitated for at least 2, preferably at least 3, more preferably at least 5 hours, though in one alternative embodiment. the solution is left to sit undisturbed for that amount of time. Preferably, the temperature may be maintained as mentioned previously, though in one embodiment, the solution is left at room temperature. Following the addition of the oxidizing agent, polyaniline nanoparticles may be formed. The polyaniline nanoparticles may be removed from the solution and washed with distilled water and/or an alcohol. The polyaniline nanoparticles may be dried at 55-100° C., preferably 60-90° C. more preferably 65-80° C. at a pressure of 0.001-10 mbar, preferably 0.001-1 mbar, more preferably 0.001-0.5 mbar, for at least 15 hours, preferably at least 20 hours, more preferably at least 25 hours. In an alternative embodiment, the polyaniline nanoparticles may be dried under a vacuum at room temperature or in an oven at atmospheric pressure.

The cerium oxide and polyaniline nanoparticles synthesized by the above method may have a band gap energy of 2.20-2.50 eV, preferably 2.25-2.45 eV, more, preferably 2.30-2.40 eV. This band gap energy may also be known as the "electronic" or "electrical" band gap energy. The nanoparticles may comprise 50-90%, 60-85%, preferably 60-75% cerium oxide by mass, with the remaining mass comprising polyaniline. The polyaniline may have an oxidation state and average molecular weight as previously described. The cerium oxide and polyaniline composite nanoparticles may or may not be mesoporous or microporus. Preferably the shapes of the cerium oxide and polyaniline composite nanoparticles are substantially uniform, meaning that the height of the surface varies less than 10 nm, preferably less than 8 nm, more preferably less than 5 nm from the surface of a geometric sphere having the same center and enclosing an equivalent volume. In an alternative embodiment, the nanoparticles may have an ellipsoidal, an oblong, an ovoid, or some other rounded shape. Preferably the cerium oxide and polyaniline are dispersed evenly throughout each nanoparticle, though in one embodiment, a higher concentration of cerium oxide may exist in certain regions of a particle. In an alternative embodiment, the cerium oxide may be present as agglomerates of particles between polyaniline molecules, where the term "agglomerates" was defined previously. Here, the primary particles of the agglomerates may be cerium oxide nanoparticles. These agglomerates may have a largest dimension of 4-40 nm, preferably 4-30 nm, more preferably 6-10 nm.

In another alternative embodiment, cerium oxide nanoparticles having diameters or largest widths and surface areas as mentioned previously may be used in place of the cerium oxide composite nanospheres for the photocatalytic conversion of an aromatic nitro compound into an aromatic amine compound. The cerium oxide nanoparticles used for this purpose may be synthesized by the previously described method, or obtained by other means. In one embodiment, a mixture of both cerium oxide and polyaniline composite nanospheres and nanoparticles may be used as photocatalysts, for example, in a reaction solution at a mass ratio of nanospheres to nanoparticles of 10:1-1:10, preferably 5:1-1:5, more preferably 2:1-1:2. In an alternative embodiment, a mixture of cerium oxide and polyaniline composite nanomaterials with a wide size distribution may be used as a photocatalyst. For example, a reaction solution may comprise particles of cerium oxide and polyaniline composites having largest dimensions of 10-500 nm, with or without hollow cores. In another alternative embodiment, agglomerates of the cerium oxide and polyaniline nanospheres and/or nanoparticles may be used as photocatalysts. In another alternative embodiment, polyaniline nanospheres and/or nanoparticles without cerium oxide may be used as photocatalysts following the above mentioned procedures. In another embodiment, the cerium oxide and polyaniline composite nanoparticles, polyaniline nanoparticles, and/or polyaniline nanospheres may be recovered from a reaction solution and reused as photocatalysts. In another alternative embodiment, cerium oxide and polyaniline nanocomposites in different forms may be used as photocatalysts as described above. For example, a nanocomposite may be created by polymerizing aniline onto the surface of cerium oxide nanoparticles, creating a core-shell structure. Alternatively, cerium oxide and polyaniline may be deposited as a nanocomposite on a silica support or an ITO glass electrode, and then used as a photocatalyst. In a related alternative embodiment, a cerium oxide and polyaniline nanocomposite may be confined within a flow cell to continuously deliver a solution of an aromatic nitro compound, irradiate the solution in the presence of the photocatalyst, and remove irradiated solution containing the aromatic amine compound. In this alternative embodiment, the photocatalyst may be fixed to a solid, stationary support within the flow cell.

The examples below are intended to further illustrate protocols for preparing, characterizing, and using cerium oxide and polyaniline composite nanospheres and nanoparticles and are not intended to limit the scope of the claims.

EXAMPLE 1

Preparation of Photocatalysts

Materials
Aniline monomer (99% purity, Aldrich), cerium isopropoxide, polyvinylpyrrolidone (PVP, average molecular weight of 360 kDa) ammonium persulfate (APS), sodium dodecylbenzenesulfonate (SDBS), ethanol (99.8%), n-butyl alcohol (BA), and hydrochloric acid (HCl, 37%) were used as received without further purification.

Preparation of Polyaniline Atmospheres
The microemulsion method was employed to prepare polyaniline nanospheres (PANI_NS). In this procedure 6.0 g of sodium dodecyl benzene sulfonate (SDBS) was dissolved in 100 mL of distilled water while maintaining, a pH of 0.3 with the addition of HCl solution. 1.3 mL of aniline monomer was added to the mixture. After stirring for 60 min, 4 mL of n-butyl alcohol (BA) was added drop-wise to the mixture. The temperature of the mixture was adjusted to 25° C., and a 33 mL solution of 10 mass % ammonium persulfate (APS) in water was added and stirred for an additional 5 h to achieve polymerization of the aniline monomer. A change of color from brown-yellow to dark-green was observed during the stirring process. The mixture was washed several times with distilled water and ethanol, and dried for 12 h at 70° C. using a vacuum oven to collect PANI_NS.

Preparation of Polyaniline Nanoparticles
A chemical oxidative polymerization of aniline was employed to prepare polyaniline nanoparticles (PANI_NP). In this procedure 1.3 mL of aniline monomer was added to 100 mL of HCl aqueous solution under vigorous stirring at 1° C. with HCl added to maintain a pH of 0.3. A 33 mL volume of 10% APS solution was added to the mixture and stirred for 5 h. The mixture was washed several times with distilled water and ethanol under vacuum. The product was dried for 30 h at 70° C. using a vacuum oven to collect PANI_NP for further use.

Preparation of $CeO_2$@PANI Nanocomposites
A mixture of 0.3 g of PVP and 1.6 g of PANI_NS or PANI_NP were dispersed in 30 mL of ethanol using an ultrasonic bath for 60 min. Then, 100 mL cerium isopropoxide solution (0.3 mol/L cerium isopropoxide in ethanol) was added to the mixture with further dispersion in the ultrasonic bath for 3 hrs. The mixture was washed several times with distilled water and ethanol under vacuum distillation. The mixture was dried for 24 h at 100° C. The product was calcined for 4 h at 350° C. In this way either $CeO_2$@PANI_NS or $CeO_2$@PANI_NP were prepared. For comparison p poses pure $CeO_2$ nanospheres ($CeO_2$ NS) were prepared by the above-mentioned procedures without the use of PANI_NS or PANI_NP.

EXAMPLE 2

Characterization

Physical Characterization
A JEOL-JEM-1230 transmission electron microscope (TEM) was used to obtain the morphology and sample dimensions of the prepared materials. To get the TEM images, samples were ultrasonicated for 30 min after suspension in ethanol. A small portion of the suspended sample was dried on a carbon-coated copper grid and loaded into the TEM.

The surface area of the samples was calculated from $N_2$-adsorption measurements using a Nova 2000 series Chromatech apparatus at 77 K. Samples were heated at 100° C. under vacuum for 2 h to complete this measurement.

A Bruker Axis D8 X-ray diffraction (XRD) system was used to observe the crystalline phase of the nanocomposites by employing Cu Kα radiation (λ=1.540 Å) at room temperature.

A Thermo-Scientific K-ALPHA spectrometer was used to obtain X-ray photoelectron spectroscopy (XPS) measurements. A UV-Vis-NIR spectrophotometer (V-570, Jasco, Japan) was used to record ultraviolet-visible diffuse reflectance spectra (UV-Vis-DRS) at room temperature, over the absorption range of 200-800 nm. Band gap performance was determined from the observed UV-Vis-DRS. A Shimadzu RF-5301 fluorescence spectrophotometer was used to record photoluminescence emission spectra (PL). Transmittance mode FTIR spectra were recorded for a solid mixture of the sample and KBr using a JASCO FTIR-6000 spectrometer at a spectral resolution of 2 cm$^{-1}$ to take 100 scans at room temperature.

Photocatalytic Tests

The efficiencies of the prepared nanocomposites were tested with the reduction of nitrobenzene into aniline. For this purpose, a known weight of the photocatalyst was ultrasonically dispersed in a 10 mL nitrobenzene-CH$_3$OH solution (1/99, v/v) with the initial concentration of nitrobenzene (NB) at 8.13×10$^{-4}$ mol/L. The reaction mixture was illuminated under visible light produced from a 500 W xenon lamp mounted on a photocatalytic reactor. A λ>420 nm cutoff filter was used, and a tube of running water was exploited to prevent heating and maintain the reaction solution at approximately 30° C. The sealed quartz reactor was positioned 11 cm from the light source. Before illumination, the solution was flushed with nitrogen gas for 0.5 h to remove dissolved oxygen. The illumination time was set at 2.5 h for each experiment. After exposure, samples were drawn from the reactor, centrifuged at 7000 rpm for 20 min, and finally filtered through a 0.2-μm Millipore filter to remove any residual particles. An Agilent GC 7890A model G3440A Gas Chromatograph was used to analyze the resulting aniline from the reduction process.

EXAMPLE 3

Results and Discussion

Characterizations of Materials

FIG. 1 shows XRD patterns of PANI_NP, PANI_NS, CeO$_2$NS, CeO$_2$@PANI_NP and CeO$_2$@PANI_NS samples. The broad peak at ~15-25° suggests polyaniline phase structure for PANI_NP and PANI_NS. On the other hand, CeO$_2$NS, CeO$_2$@PANI_NP, and CeO$_2$@PANI_NS are composed of CeO$_2$ phase as the characteristic peak of polyaniline disappears in the spectra of CeO$_2$@PANI_NP and CeO$_2$@PANI_NS. Also, the decrease in the intensity of the characteristic peaks of the CeO$_2$ phase in the spectra of CeO$_2$@PANI_NP and CeO$_2$@PANI_NS suggests that doping of polyaniline decreases crystallite sizes of both composites.

Figure 2A:
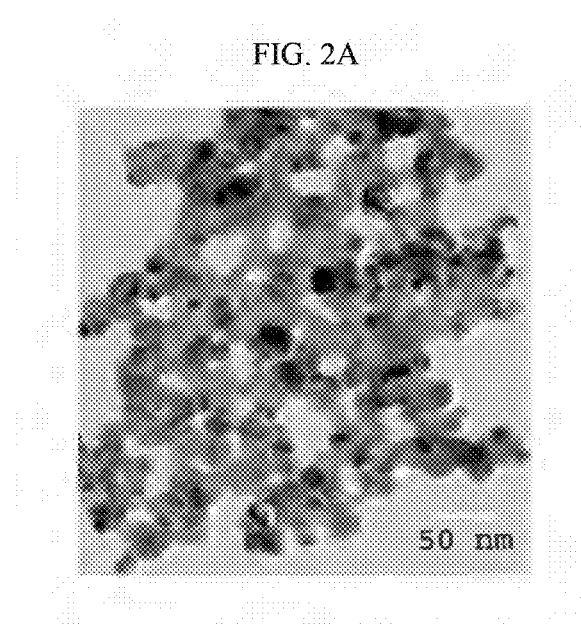
FIG. 2A is a transmission electron microscopy (TEM) image of PANI_NP.
Figure 2B:
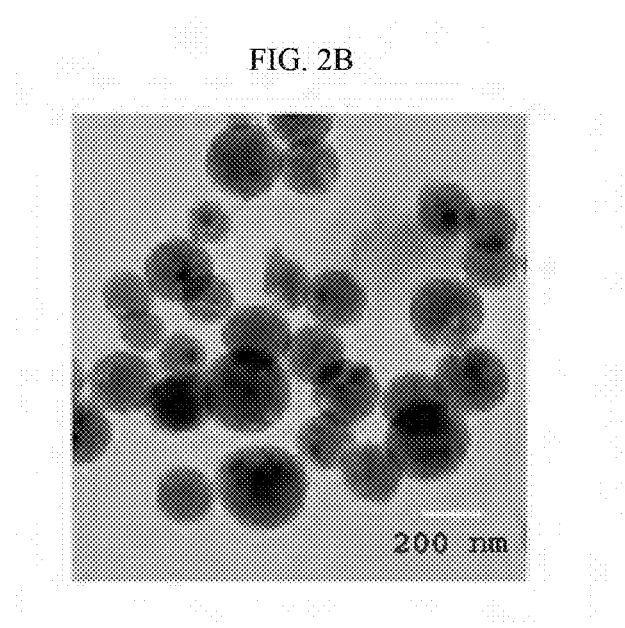
FIG. 2B is a TEM image of PANI_NS.
Figure 2D:
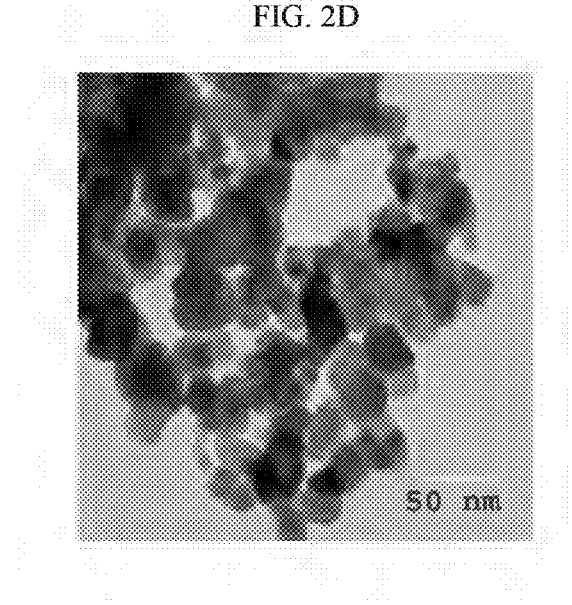
FIG. 2D is a TEM image of $CeO_2$@PANI_NP.
Figure 2E:
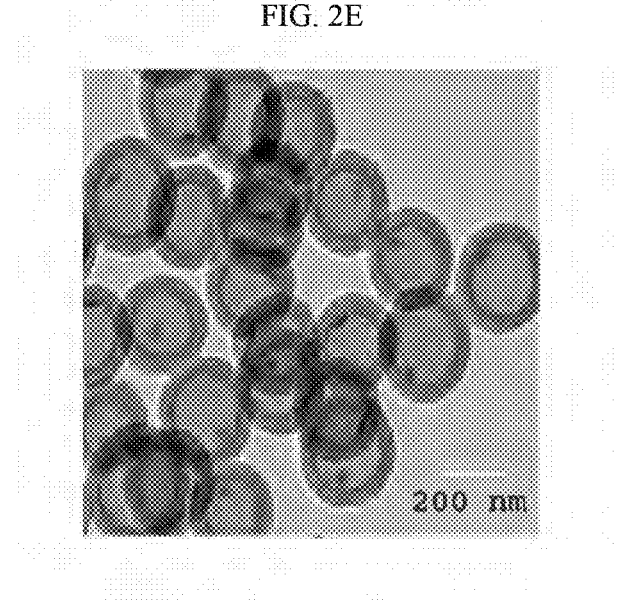
FIG. 2E is a TEM image of $CeO_2$@PANI_NS.

FIG. 2A-2E shows TEM images of PANI_NP (FIG. 2A), PANI_NS (FIG. 2B), CeO$_2$NS (FIG. 2C). CeO$_2$@PANI_NP (FIG. 2D), and CeO$_2$@PANI_NS (FIG. 2E) samples. PANI_NP and CeO$_2$@PANI_NP are nanoparticles in shape with sizes of 60 and 75 nm, respectively. However, CeO$_2$NS, PANI_NS, and CeO$_2$@PANI_NS are nanospherical in shape with shell thicknesses of 20-40, 22-44, and 25-50 nm, respectively, and core diameters of 150, 170, and 190 nm, respectively. The addition of polyaniline increases the size of CeO$_2$@PANI_NS particles.

Figure 3A:
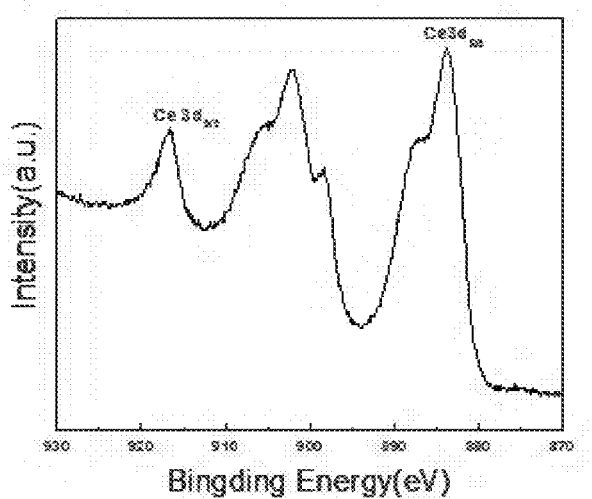
FIG. 3A is an X-ray photoelectron spectroscopy (XPS) spectrum of $CeO_2$@PANI_NS showing Ce $3d_{5/2}$ and Ce $3d_{3/2}$ binding peaks.
Figure 3B:
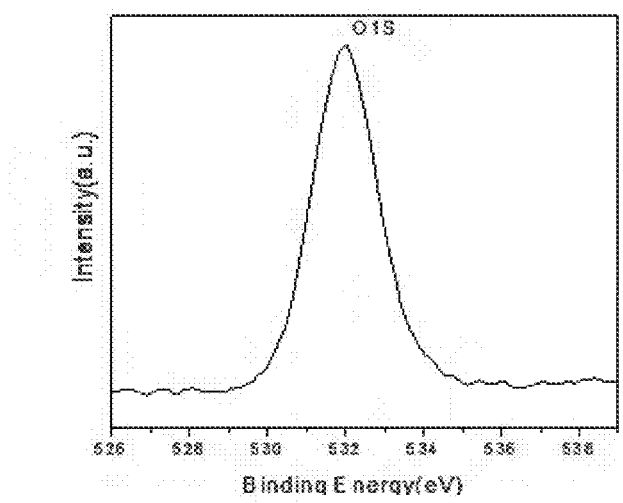
FIG. 3B is an XPS spectrum of $CeO_2$@PANI_NS showing an O 1s binding peak.
Figure 3C:
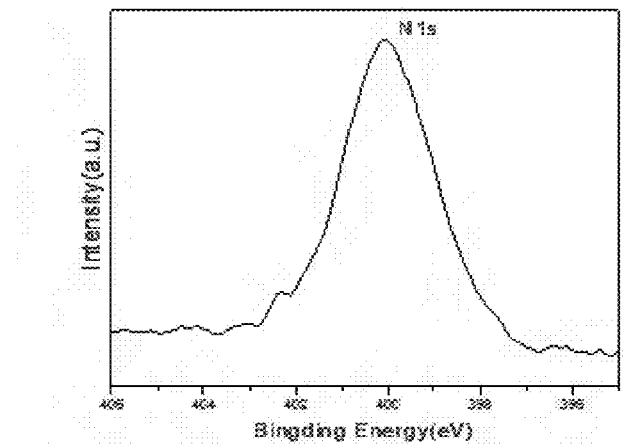
FIG. 3C is an XPS spectrum of $CeO_2$@PANI_NS showing a N 1s binding peak.
Figure 3D:
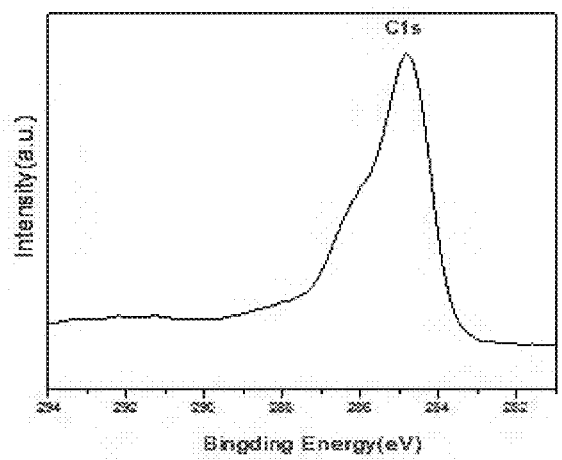
FIG. 3D is an XPS spectrum of $CeO_2$@PANI_NS showing a C 1s binding peak.

FIG. 3A-3D shows XPS spectra of the CeO$_2$@PANI_NS sample for Ce 3d (FIG. 3A), O 1s (FIG. 3B), N 1s (FIG. 3C), and C 1s (FIG. 3D) binding peaks. The presence of two binding peaks for Ce 3d$_{5/2}$ at 882 eV and Ce 3d$_{3/2}$ at 916 eV indicate that the cerium ion is Ce(IV) (FIG. 3A). The presence of one binding peak for O 1s at 531.6 eV (FIG. 3B) indicates that oxygen ion is present as O$^{2-}$. Therefore, The XPS results for O 1s and Ce 3d confirm the presence of CeO$_2$. XPS spectra for N 1s and C 1s confirm the presence of aniline in the CeO$_2$@PANI_NS sample, due to the presence of the binding peaks for N 1s and C 1s at 400 and 284.7 eV, as shown in FIGS. 3C and 3D, respectively.

Figure 4:
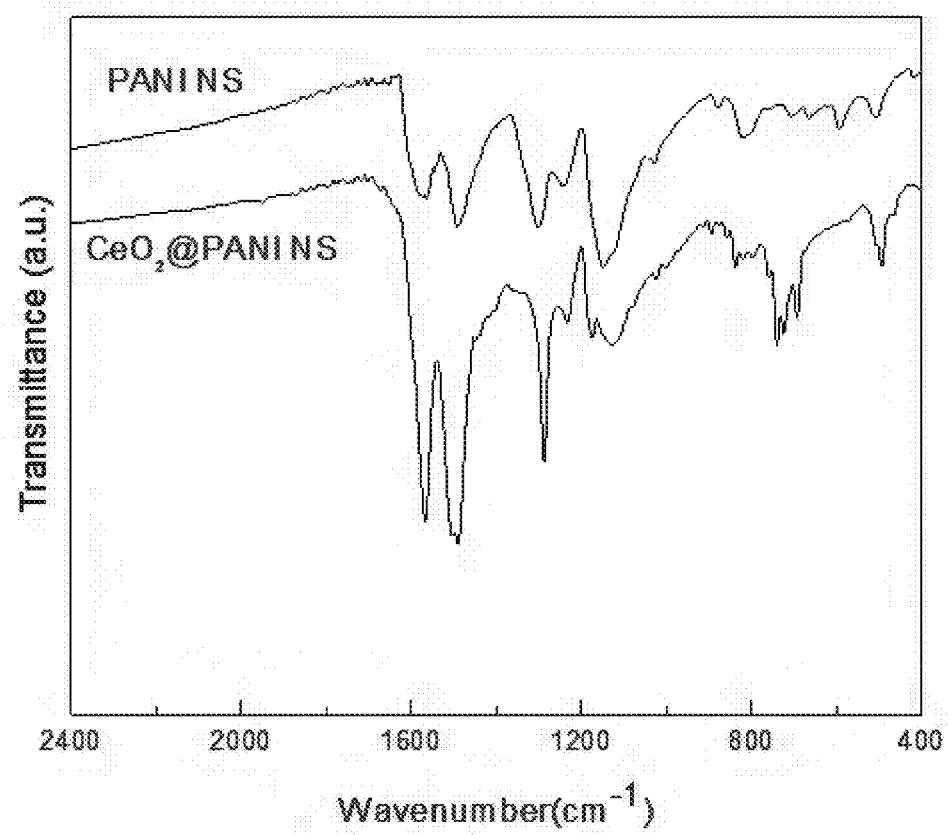
FIG. 4 shows FT-IR spectra for PANI_NS and $CeO_2$@PANI_NS.

FIG. 4 shows FT-IR spectra for PANI_NS and CeO$_2$@PANI_NS samples. The characteristic peaks at 1567, 1492, 1297, 1245, 1147, and 815 cm$^{-1}$ for polyaniline are present in both PANI_NS and CeO$_2$@PANI_NS samples, which confirm the presence of polyaniline in CeO$_2$@PANI_NS samples.

Figure 5A:
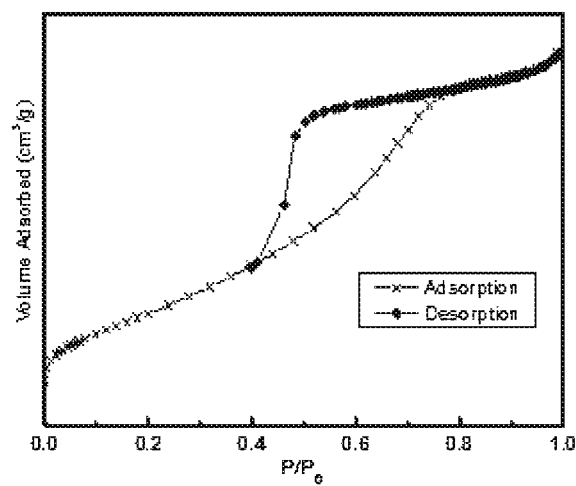
FIG. 5A shows an adsorption-desorption isotherm of $CeO_2$_NS.
Figure 5B:
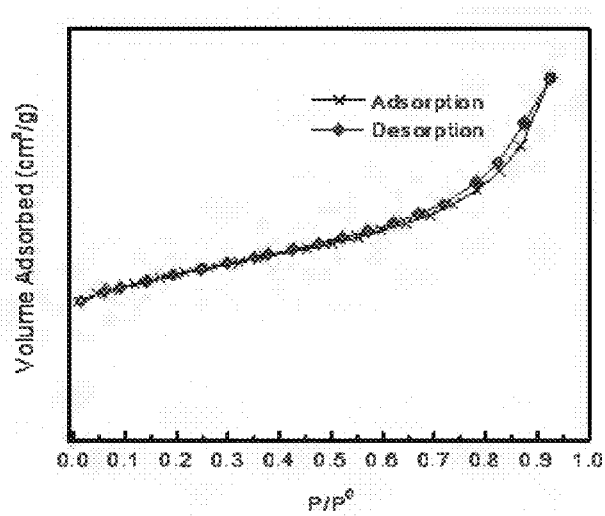
FIG. 5B shows an adsorption-desorption isotherm of $CeO_2$@PANI_NP.
Figure 5C:
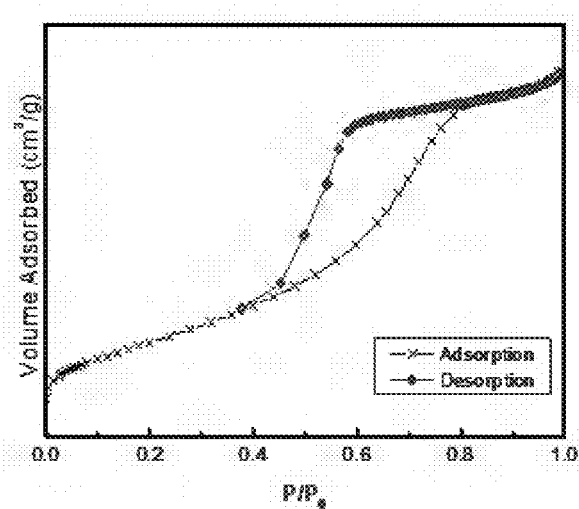
FIG. 5C shows an adsorption-desorption isotherm of $CeO_2$@PANI_NS.

FIGS. 5A, 5B, and 5C show adsorption-desorption isotherms of CeO$_2$ NS, CeO$_2$@PANI_NP, and CeO$_2$@PANI_NS, respectively. A type II isotherm is present for the CeO$_2$@PANI_NP sample as shown in FIG. 5B. A type IV isotherm is present for both CeO$_2$ NS and CeO$_2$@PANI_NS samples as shown in FIGS. 5A and 5C, respectively. Therefore, CeO$_2$ NS and CeO$_2$@PANI_NS samples are mesoporous materials.

Figure 6:
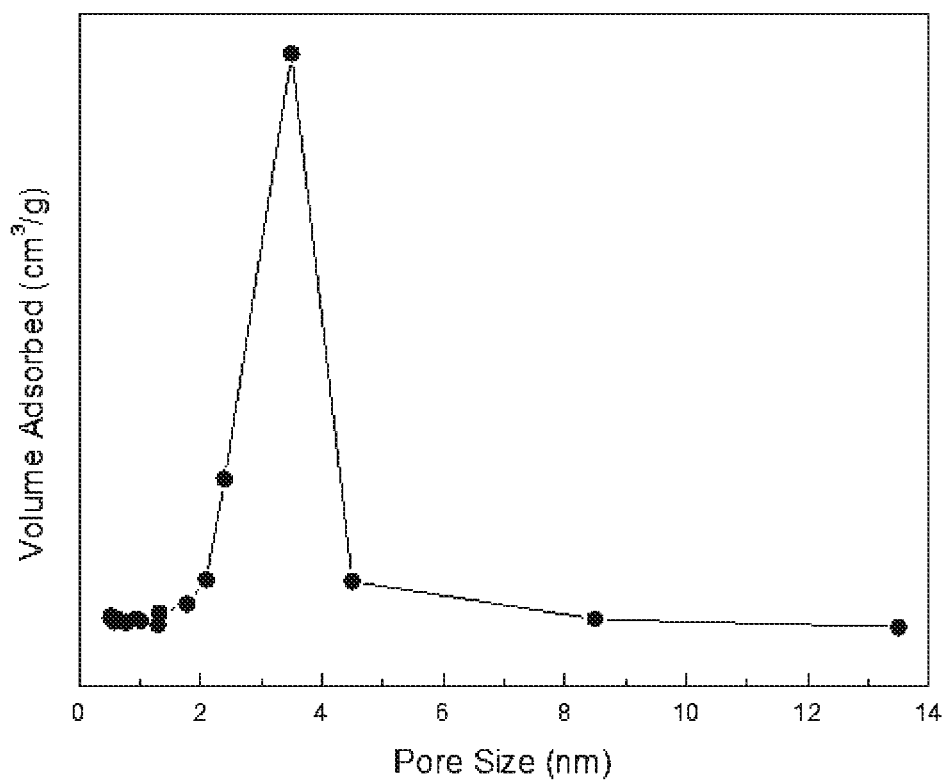
FIG. 6 shows the pore size distribution of $CeO_2$@PANI_NS.

FIG. 6 shows pore size distribution of a CeO$_2$@PANI_NS sample with a narrow distribution of pore sizes around 3.5 nm. This explains that the core-shell structure has a high surface area. The values of specific surface area of PANI_NS, CeO$_2$@PANI_NS, PANI_NP, CeO$_2$@PANI_NP, and CeO$_2$ NS as calculated from desorption measurements are 200, 260, 40, 110, and 130 m$^2$/g, respectively.

Figure 7:
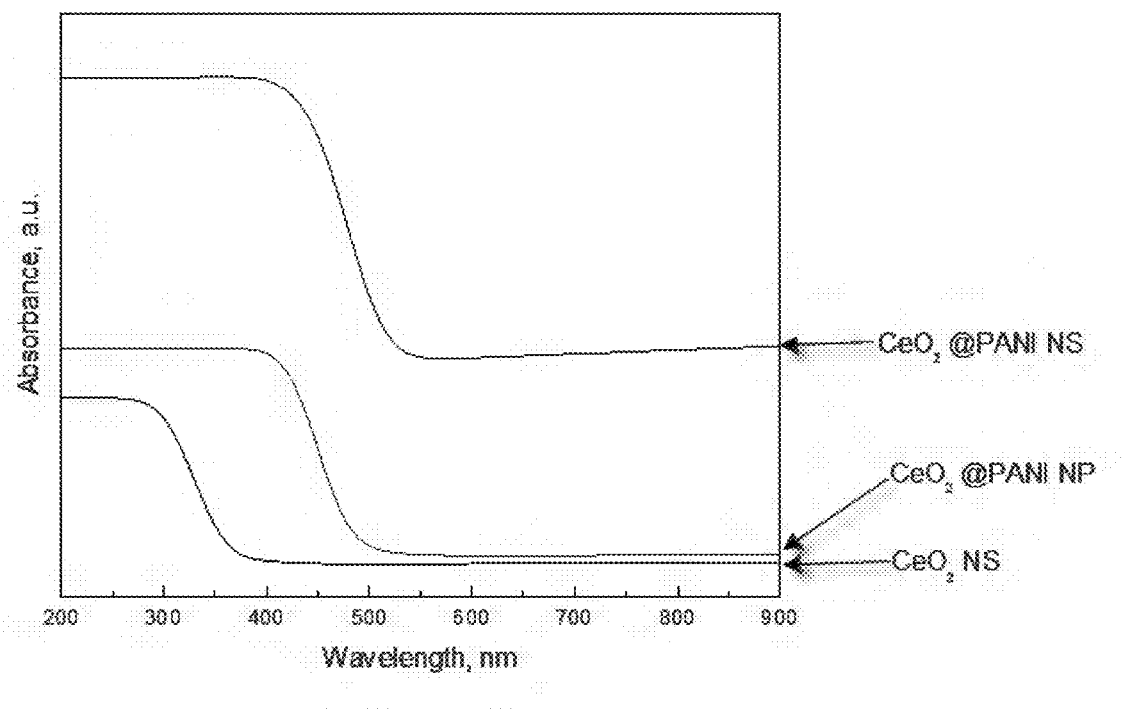
FIG. 7 shows UV-Vis spectra of $CeO_2$_NS, $CeO_2$@PANI_NP, and $CeO_2$@PANI_NS samples.

FIG. 7 shows UV-Vis spectra of CeO$_2$ NS, CeO$_2$@PANI_NP, and CeO$_2$@PANI_NS samples. The curve shows that CeO$_2$ NS absorbs in the UV region. The addition of polyaniline to nanoparticles and to nanospheres results in a shift of the cerium dioxide absorption edge from the UV to the visible region. Furthermore, the shift is greater in the case of polyaniline nanospheres. The values of band gap energies as calculated from the UV-Vis spectra of CeO$_2$ NS, CeO$_2$@PANI_NP, and CeO$_2$@PANI_NS are 3.21, 2.38, and 1.91 eV, respectively.

Figure 8:
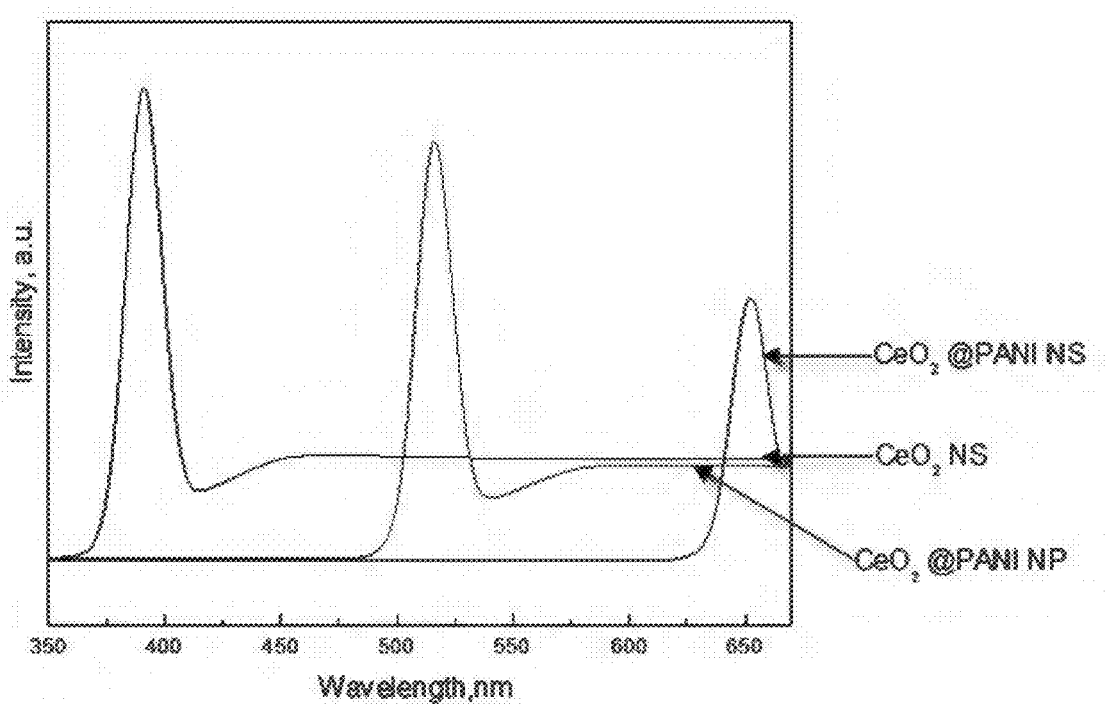
FIG. 8 is photoluminescence (PL) spectra of $CeO_2$_NS, $CeO_2$@PANI_NP, and $CeO_2$@PANI_NS samples.

FIG. 8 shows PL spectra of CeO$_2$ NS, CeO$_2$@PANI_NP, and CeO$_2$@PANI_NS samples. CeO$_2$ NS shows high PL peak intensity. The addition of polyaniline to the nanoparticles and nanospheres decreases the PL peak intensity. Furthermore, the decrease in case of polyaniline nanospheres is greater than that of polyaniline nanoparticles. The values of band gap energies of CeO$_2$ NS, CeO$_2$@PANI_NP, and CeO$_2$@PANI_NS samples as calculated from their PL emission spectra are 3.20, 2.37, and 1.90 eV, respectively. These band gap energies are very close to those obtained from UV-Vis spectra as discussed in the previous paragraph.

Photocatalytic Performance

Figure 9:
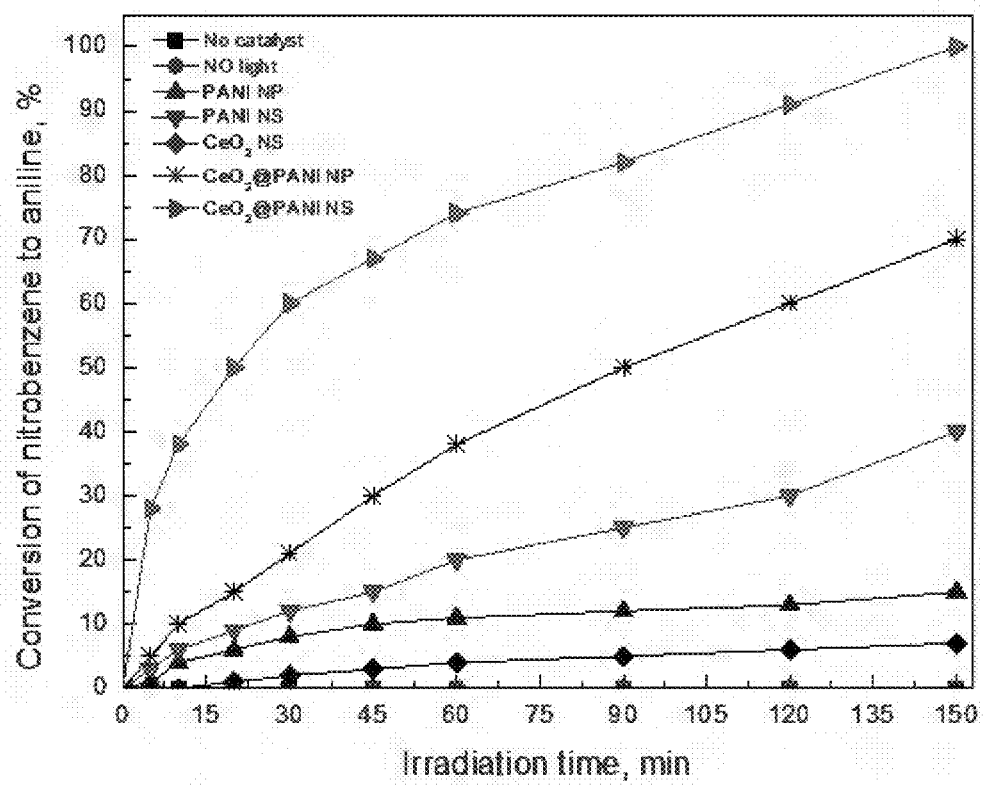
FIG. 9 shows the conversion rate over time of different photocatalysts.

As mentioned earlier, the reaction of nitrobenzene into aniline was utilized to test the activity of the synthesized photocatalyst. A comparison between various prepared structures was performed. FIG. 9 shows the effect of the type of photocatalyst on the reaction of nitrobenzene to aniline. The photocatalytic conversion of nitrobenzene to aniline with the use of CeO$_2$ NS is very small (7%), and this can be explained by the fact that CeO$_2$ NS absorbs only in the UV region while the light source used is in the visible region. Photocatalytic conversion of nitrobenzene to aniline with the use of PANI_NP and PANI_NS was at 15% and 40%, respectively. Photocatalytic conversion of nitrobenzene to aniline with the use of CeO$_2$@PANI_NP and CeO$_2$@PANI_NS as photocatalysts was at 70% and 100%, respectively. It is clear that the addition of polyaniline nanoparticles and nanospheres increases the photocatalytic conversion of nitrobenzene to aniline. Polyaniline naonospheres in the form of CeO$_2$@PANI_NS exhibit superior efficiency with about 100% conversion.

Figure 10:
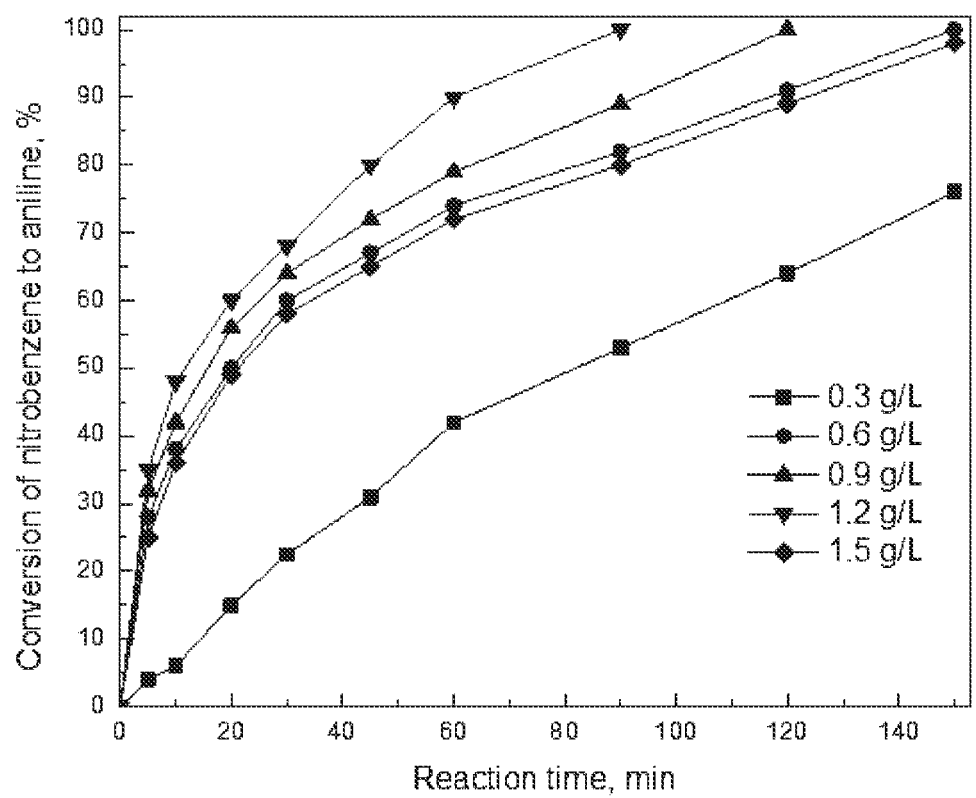
FIG. 10 shows the effect of the dose of the CeO2@PANI_NS photocatalyst on the conversion of nitrobenzene to aniline.

The effect of the amount of added catalyst to the reaction was also studied. FIG. 10 shows the effect of the dose of the CeO$_2$@PANI_NS photocatalyst on the conversion of nitrobenzene to aniline. The photocatalytic conversion rate increased from 75% to 100% by increasing the dose from 0.3 to 0.6 g/L, respectively. Reaction time required for a complete conversion of nitrobenzene to aniline decreased from 150 to 90 min by increasing the dose of CeO$_2$@PANI_NS from 0.6 to 1.2 g/L. This may be due to an increased number of available active sites by the increase in the dose of the photocatalyst. However, if the dose is increased from 1.2 g/L to 1.5 g/L, the photocatalytic conversion of nitrobenzene to aniline decreases from 100% to 98%, and the reaction time increases from 90 to 150 min. The higher dose of the photocatalyst may limit the penetration of light to all active sites within the dispersed photocatalyst.

Figure 11:
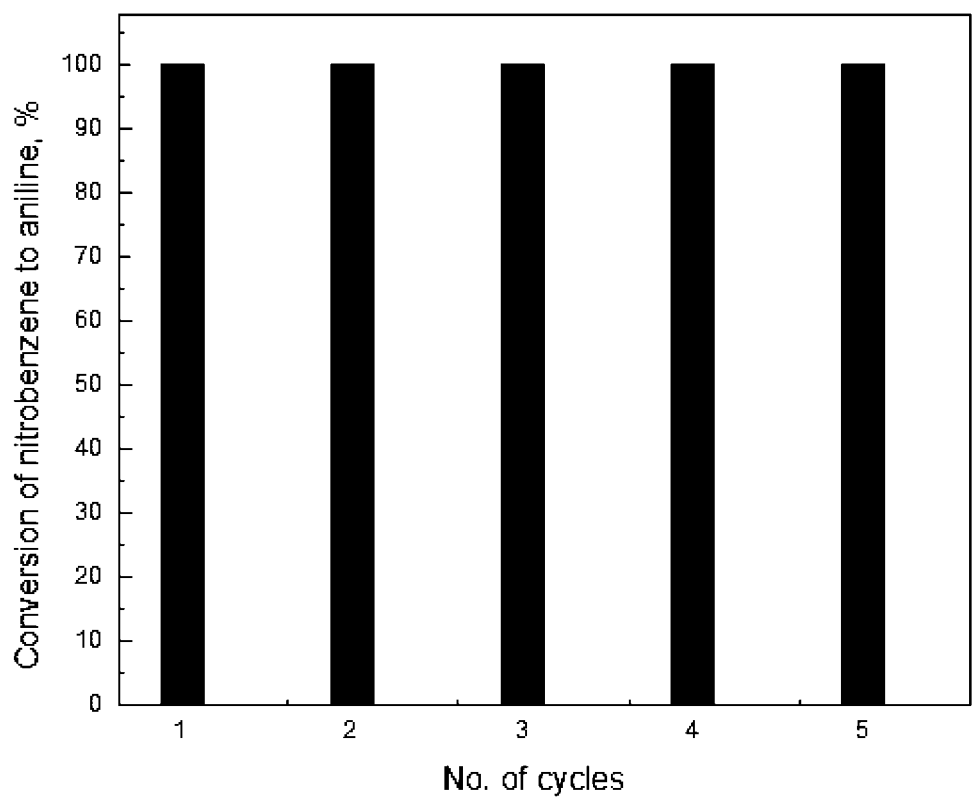
FIG. 11 shows the conversion activity of the photocatalyst when reused.

A test on the possibility of reusing the catalyst was also performed. FIG. 11 shows recycling and reuse of the CeO$_2$@PANI_NS photocatalyst for the reaction of nitrobenzene to aniline. The figure shows that the conversion remains constant even if the catalyst was used a total of five times, showing great stability of the CeO$_2$@PANI_NS photocatalyst.

Polyaniline nanospheres were prepared by a microemulsion method. Polyaniline nanoparticles were prepared by chemical oxidative polymerization of aniline. CeO$_2$@PANI_NS was prepared by a method that ensures the production of a uniform spherical core-shell structure. The photocatalytic performance of the nanocomposites was studied by the photocatalytic reduction of nitrobenzene to aniline under visible light. The values of specific surface area of PANI_NS, CeO$_2$@PANI_NS, PANI_NP, CeO$_2$@PANI_NP, and CeO$_2$ NS are 200, 260, 40, 110, and 130 m$^2$/g, respectively, which means that the NS structures have the higher specific surface areas. The shapes of PANI_NS (nanospheres), CeO$_2$@PANI_NS (core-shell nanospheres), PANI_NP (nanoparticles), CeO$_2$@PANI_NP (nanoparticles), and CeO$_2$ NS (nanospheres); were determined by TEM. The photocatalytic performance of CeO$_2$@PANI_NS for reduction of nitrobenzene to aniline under visible light is 1.4, 2.5, 6.6, and 14.3 times more than that of CeO$_2$@PANI_NP, PANI_NS, PANI_NP, and CeO$_2$ NS, respectively.

The invention claimed is:

1. A method of making cerium oxide and polyaniline composite nanospheres comprising a spherical shell, the method comprising:
   mixing aniline monomers with water, a first alcohol, and a surfactant to form a first mixture,
   adding an oxidizing agent to the first mixture to polymerize the aniline monomers to form polyaniline nanospheres,
   mixing the polyaniline nanospheres with a water soluble polymer, a cerium alkoxide and a second alcohol to form a second mixture, and
   heating the second mixture at 300-400° C. to form the cerium oxide and polyaniline composite nanospheres, wherein each shell has a thickness of 5-60 nm and surrounds a hollow core having a 70-300 nm diameter.

2. The method of claim 1, wherein a molar ratio of the aniline monomers to the surfactant is 0.6-1.0.

3. The method of claim 1, wherein the surfactant is a sulfonic acid derivative.

4. The method of claim 3, wherein the surfactant is sodium dodecylbenzenesulfonate.

5. The method of claim 1, wherein the first alcohol has a molecular weight of 30-40 g/mol and a boiling point of 60-180° C.

6. The method of claim 5, wherein the first alcohol is n-butanol.

7. The method of claim 1, wherein the oxidizing agent is at least one persulfate salt selected from the group consisting of ammonium persulfate, sodium persulfate, and potassium persulfate.

8. The method of claim 1, wherein the water soluble polymer is polyvinylpyrrolidone, and a mass ratio of the polyaniline nanospheres to polyvinylpyrrolidone in the second mixture is 3.0-8.0.

9. The method of claim 1, wherein the cerium alkoxide is cerium isopropoxide.

10. The method of claim 1, wherein a mass ratio of cerium to polyaniline nanospheres in the second mixture is 1.5-3.5.

11. The method of claim 1, wherein the cerium oxide and polyaniline composite nanospheres have a porous surface with a surface area of 220-300 m$^2$/g and an average pore diameter of 1.5-5.0 nm.

12. The method of claim 1, wherein the cerium oxide and polyaniline composite nanospheres have a band gap energy of 1.75-2.05 eV.

* * * * *